United States Patent

Baudoin et al.

[11] Patent Number: 5,889,053
[45] Date of Patent: Mar. 30, 1999

[54] FARNESYL TRANSFERASE INHIBITORS, PREPARATION THEREOF AND PHARMACEUTICALS COMPOSITIONS CONTAINING SAID INHIBITORS

[75] Inventors: Bernard Baudoin, Chaville, France; Christopher Burns, Rosemont, Pa.; Alain Commercon, Vitry-sur-Seine; Alain Lebrun, Vigneux, both of France

[73] Assignee: Rhone-Poulenc Rorer S.A., Antony, France

[21] Appl. No.: 5,154

[22] Filed: Jan. 9, 1998

[30] Foreign Application Priority Data

Jul. 12, 1995 [FR] France .................................. 95 08423

[51] Int. Cl.⁶ .................................................. A61K 31/235
[52] U.S. Cl. .......................... 514/542; 514/502; 560/10; 562/427
[58] Field of Search ............................... 562/427; 460/10; 514/542, 562

[56] References Cited

U.S. PATENT DOCUMENTS 5,705,686  1/1998  Sebti et al. .............................. 562/557

*Primary Examiner*—Samuel Barts
*Attorney, Agent, or Firm*—Raymond S. Parker, III

[57] ABSTRACT

Novel farnesyl transferase inhibitors of general formula (I),

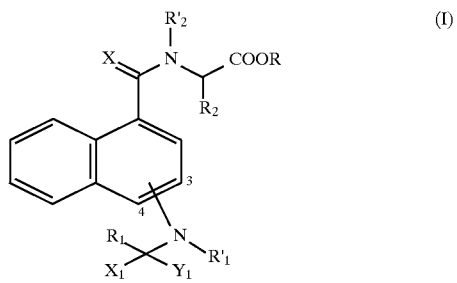

the preparation thereof and pharmaceutical compositions containing said inhibitors, are disclosed. In general formula (I), $R_1$ is $Y—S—A_1$ (where Y is a hydrogen atom, an amino acid residue, a fatty acid residue, an alkyl or alkoxycarbonyl radical or a radical $R_4$—S— where $R_4$ is a $C_{1-4}$ alkyl radical optionally substituted by a phenyl radical or a radical of general formula (II)

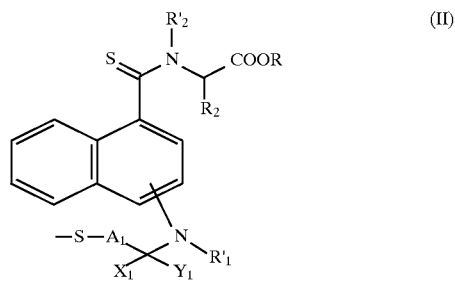

wherein $A_1$, X, $X_1$, $Y_1$, $R'_1$, $R_2$, $R'_2$ and R are defined as below, and $A_1$ is a $C_{1-4}$ alkylene radical optionally alpha-substituted in the $>C(X_1)(Y_1)$ grouping by an amino or alkylamino, dialkylamino, alkanoylamino or alkoxycarbonylamino radical); $X_1$ and $Y_1$ are each a hydrogen atom or, taken together with the carbon atom to which they are attached, form a $>C=O$ grouping; $R'_1$ is hydrogen or a $C_{1-6}$ alkyl radical; X is an oxygen or sulphur atom; $R_2$ is a $C_{1-6}$ alkyl, alkenyl or alkynyl radical optionally substituted by hydroxyl, alkoxy, mercapto, alkylthio, alkylsulphinyl or alkylsulphonyl, with the proviso that when $R_2$ is an alkyl radical substituted by a hydroxy radical, $R_2$ can form a lactone with the α-carboxy radical; and $R'_2$ is hydrogen or a $C_{1-6}$ alkyl radical; and R is a hydrogen atom or an optionally substituted alkyl radical or an optionally substituted pheny radical, with the proviso that radical (a)

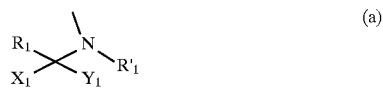

is in the 3 or 4 position of the naphthyl ring. The novel products have anticancer properties.

8 Claims, No Drawings

FARNESYL TRANSFERASE INHIBITORS, PREPARATION THEREOF AND PHARMACEUTICALS COMPOSITIONS CONTAINING SAID INHIBITORS

This application is a continuation of international application number PCT FR96/01071, filed 10 Jul. 1996.

The present invention relates to new farnesyl transferase inhibitors of general

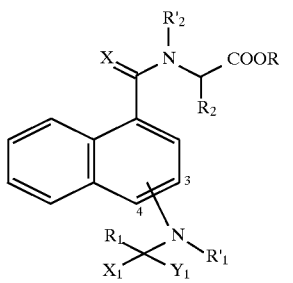

optionally to their salts, to their preparation and to the pharmaceutical compositions which contain them.

The inhibition of farnesyl transferase, and consequently of the farnesylation of the Ras protein, blocks the capacity of the mutated Ras protein to transform normal cells into cancerous cells.

The C-terminal sequence of the Ras gene contains the unit "CAAX" or "Cys-Aaa$_1$-Aaa$_2$-Xaa", in which Aaa represents an aliphatic amino acid and Xaa represents any amino acid.

It is known that tetrapeptides with a CAAX sequence can inhibit the farnesylation of the Ras protein. For example, peptide inhibitors of farnesyl transferase, Cys-Aaa$_1$-Aaa$_2$-Xaa, which are especially represented by the peptides Cys-Val-Leu-Ser, Cys-Val-Ile-Met and Cys-Val-Val-Met which manifest their inhibitory activity at concentrations in the region of $10^{-6}$M or of $10^{-7}$M, have been described in PCT Application WO 91/16340 and in Application EP 0,461,869.

It has now been found, and this forms the subject of the present invention, that the peptides of general formula (I) manifest their inhibitory activity (IC$_{50}$) at concentrations of the order of $10^{-8}$ or of $10^{-9}$M.

In the general formula (I),

R$_1$ represents a radical of general formula Y—S—A$_1$— in which Y represents a hydrogen atom or an amino acid residue or a fatty acid residue or an alkyl or alkoxycarbonyl radical or an R$_4$—S— radical in which R$_4$ represents an alkyl radical containing 1 to 4 carbon atoms, optionally substituted by a phenyl radical, or a radical of general formula:

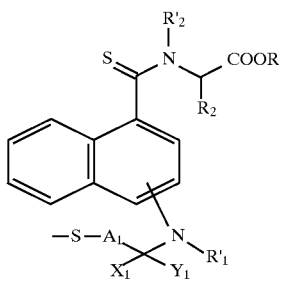

in which A$_1$, X, X$_1$, Y$_1$, R'$_1$, R$_2$, R'$_2$ and R are defined as below, and A$_1$ represents a straight or branched alkylene radical containing 1 to 4 carbon atoms, optionally substituted at the position α to the >C(X$_1$)(Y$_1$) group by an amino radical, an alkylamino radical containing 1 to 6 straight- or branched-chain carbon atoms, a dialkylamino radical in which each alkyl part contains 1 to 6 straight- or branched-chain carbon atoms, an alkanoylamino radical containing 1 to 6 straight- or branched-chain carbon atoms or an alkoxycarbonylamino radical in which the alkyl part contains 1 to 6 straight- or branched-chain carbon atoms, X$_1$ and Y$_1$ each represent a hydrogen atom or form, together with the carbon atom to which they are bonded, a >C=O group, R'$_1$, represents a hydrogen atom or a straight or branched alkyl radical containing 1 to 6 carbon atoms, X represents an oxygen or sulphur atom, R$_2$ represents a straight or branched alkyl, alkenyl or alkynyl radical containing 1 to 6 carbon atoms, optionally substituted by a hydroxyl radical, an alkoxy radical containing 1 to 4 carbon atoms, a mercapto radical, an alkylthio radical containing 1 to 4 carbon atoms, an alkylsulphinyl radical containing 1 to 4 carbon atoms or an alkylsulphonyl radical containing 1 to 4 carbon atoms, it being understood that, when R$_2$ represents an alkyl radical substituted by a hydroxyl radical, R$_2$ can form a lactone with the carboxyl radical at the α position, R'$_2$ represents a hydrogen atom or a straight or branched alkyl radical containing 1 to 6 carbon atoms, and R represents a hydrogen atom or an alkyl radical containing 1 to 6 carbon atoms, optionally substituted by a radical of the type alkoxy containing 1 to 4 carbon atoms, alkylthio containing 1 to 4 carbon atoms, alkylsulphinyl containing 1 to 4 carbon atoms, alkylsulphonyl containing 1 to 4 carbon atoms, phenyl, phenoxy, phenylthio, phenylsulphinyl, phenylsulphonyl, alkylamino containing 1 to 4 carbon atoms, dialkylamino in which each alkyl part contains 1 to 4 carbon atoms, or a phenyl radical, optionally substituted by one or a number of atoms or radicals chosen from halogen atoms and alkyl, alkyloxy, alkylthio or alkanoyl radicals, it being understood that the radical

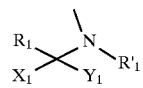

is in the 3- or 4-position of the naphthyl ring.

More particularly,

R$_1$ represents a radical of formula Y—S—A$_1$— in which Y represents a hydrogen atom or a lysine residue or a fatty acid residue containing up to 20 carbon atoms and A$_1$ represents an ethylene or propylene radical optionally substituted by an amino radical, X$_1$ and Y$_1$ each represent a hydrogen atom or form, together with the carbon atom to which they are bonded, a >C=O group, R'$_1$ represents a hydrogen atom or a methyl radical, X represents an oxygen atom, R$_2$ represents an alkyl radical containing 1 to 4 carbon atoms, optionally substituted by a hydroxyl, methoxy, mercapto, methylthio, methylsulphinyl or methylsulphonyl radical, R'$_2$ represents a hydrogen atom or a methyl radical, and R represents a hydrogen atom or an alkyl radical containing 1 to 4 carbon atoms, optionally substituted by an alkoxy radical, or a phenyl radical.

More particularly still,

R$_1$ represents a radical of formula Y—S—A$_1$— in which Y represents a hydrogen atom and A$_1$ represents an ethylene or propylene radical optionally substituted by an amino radical, $X_1$ and $Y_1$ each represent a hydrogen atom or form, together with the carbon atom to which they are bonded, a >C=O group, $R'_1$ represents a hydrogen atom, X represents an oxygen atom, $R_2$ represents a methyl, ethyl, propyl or butyl radical optionally substituted by a hydroxyl, methoxy, mercapto or methylthio radical, $R'_2$ represents a hydrogen atom, and R represents a hydrogen atom or an alkyl radical containing 1 to 4 carbon atoms.

The products of general formula (I) in which $R_1$ represents a 2-mercaptoethyl or 1-amino-2-mercaptoethyl radical, $X_1$ and $Y_1$ each represent a hydrogen atom or form, together with the carbon atom to which they are bonded, a >C=O group, $R'_1$ represents a hydrogen atom, X represents an oxygen atom, $R_2$ represents an n-butyl or 2-(methylthio) ethyl radical and $R'_2$ represents a hydrogen atom, and R represents a hydrogen atom or a methyl radical are very particularly advantageous.

The present invention also relates to the stereoisomeric forms of the products of general formula (I). The amino acid residues represented by $R_1C(X_1)(Y_1)(NR'_1)$ and $R'_2CH(NR'_2)CO$—OH preferably have the configuration of the natural amino acids.

The present invention also relates to the inorganic or organic salts of the products of general formula (I).

The new products according to the invention can be prepared by the application of known methods derived from the methods used more particularly in peptide chemistry for chain assembly.

Generally, the products of general formula (I), in which $X_1$ and $Y_1$ form, together with the carbon atom to which they are bonded, a >C=O group and X represents an oxygen atom, are obtained from 3- or 4-nitronaphthalene-1-carboxylic acid, with which is condensed an amino acid of general formula:

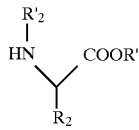
(III)

in which $R_2$ and $R'_2$ are defined as above and R' represents an alkyl radical containing 1 to 4 carbon atoms which is optionally substituted by a phenyl radical, preferably a tert-butyl radical, the reaction being carried out in the presence of a coupling agent, such as hydroxybenzotriazole and dicyclohexylcarbodiimide, and of a base, such as triethylamine, in an organic solvent, such as dimethylforinanide, in order to give a product of general formula:

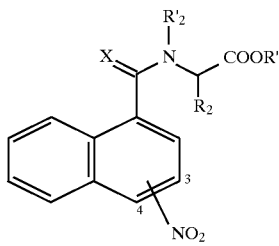
(IV)

in which X represents an oxygen atom and $R_2$, $R'_2$ and R' are defined as above, which is reduced, preferably by means of stannous chloride, to a product of general formula:

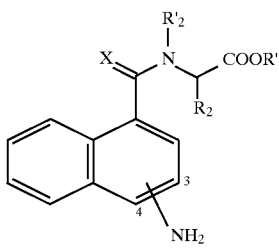
(V)

in which X represents an oxygen atom and $R_2$, $R'_2$ and R' are defined as above, with which is condensed a product of general formula:

(VI)

in which $R_1$ is defined as above and $X_1$ and $Y_1$ form, together with the carbon atom to which they are bonded, a >C=O group, it being understood that the amino and mercapto functional groups carried by $R_1$ are optionally protected by appropriate protecting groups, such as a trityl radical for the mercapto functional group or a tert-butoxycarbonyl radical for the amino functional group, the reaction preferably being carried out in the presence of an alkyl haloformate (isobutyl chloroformate) and of an organic base (N-methylmorpholine) in an inert organic solvent (tetrahydrofuran), in order to obtain a product of general formula:

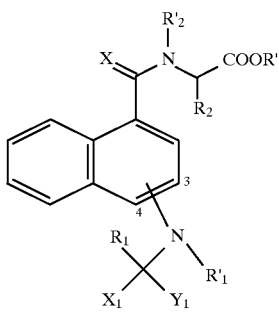
(VII)

in which the symbols X, $X_1$, $Y_1$, $R_1$, $R'_1$, $R_2$, $R'_2$ and R' are defined as above, the protective groups of which are replaced by hydrogen atoms, by means of trifluoroacetic acid in the presence of ethaneditiol, when the protective groups represent trityl, tert-butoxycarbonyl or tert-butyl radicals, in order to obtain a product of general formula (I) in which $X_1$ and $Y_1$ form, together with the carbon atom to which they are bonded, a >C=O group.

Generally, the products of general formula (I) in which the symbols $X_1$ and $Y_1$ each represent a hydrogen atom can be obtained by reaction of an aldehyde of general formula:

$R_1$—CHO  (VIII)

in which $R_1$ is defined as above, it being understood that the amino and mercapto functional groups carried by $R_1$ are optionally protected by appropriate protective groups, such as a trityl radical for the mercapto functional group or a tert-butoxycarbonyl radical for the amino functional group, with a product of general formula (VI) in the presence of a reducing agent, such as sodium cyanoborohydride, sodium borohydride, sodium triacetoxyborohydride or hydrogen in the presence of a catalyst. Generally, the reaction is carried out in an organic solvent such as an alcohol, for instance methanol, optionally in combination with another organic solvent such as an ether, for instance tetrahydrofuran. It is particularly advantageous to carry out the reaction in anhydrous medium.

Condensation of the aldehyde with the amine having been carried out, the protecting groups are replaced by hydrogen atoms by application of the usual techniques. Thus, the Boc or trityl or tert-butyl protecting groups can be replaced by hydrogen atoms by means of trifluoroacetic acid in the presence of ethanedithiol or triethylsilane.

Generally, the products of general formula (I) in which X represents a sulphur atom can be obtained from a product of general formula (IV) in which X represents an oxygen atom by thionation, generally with Lawesson's reagent, and then by carrying out the reduction, condensation or reductive amination, depending on the situation, and deprotection stages described above for the preparation of a product of general formula (I) in which X represents an oxygen atom.

When, in the general formula (I), the $R_2$ symbol forms a lactone with the carboxyl functional group in the α position, treatment in basic medium of the corresponding product leads to the product of general formula (I) in which $R_2$ represents an alkyl radical substituted by a hydroxyl radical. Generally, opening of the lactone takes place as soon as the pH becomes greater than 7. It is particularly advantageous to carry out the reaction in the presence of an inorganic base (sodium hydroxide or potassium hydroxide) in aqueous/alcoholic medium, such as a water/methanol mixture.

The products of general formula (I) in which R represents an optionally substituted alkyl radical or an optionally substituted phenyl radical as indicated above can be obtained by esterification of a product of general formula (I) in which R represents a hydrogen atom under the usual esterification conditions which do not affect the remainder of the molecule.

The products of general formula (I) in which R represents a hydrogen atom can also be obtained by saponification of a product of general formula (VI), followed by replacement of the protective groups carried by $R_1$ under the conditions described above.

3-Nitronaphthalene-1-carboxylic acid can be prepared according to the process described by T. Nakayama et al., Chem. Pharm. Bull., 32, 3968 (1984).

4-Nitronaphthalene-1-carboxylic acid can be prepared according to the process described by G. J. Leuck and R. P. Perkins, J. Amer. Chem. Soc., 51, 1831 (1929).

The products of general formula (I) can be purified according to the usual methods, such as chromatography.

The following examples illustrate the preparation of the products according to the invention.

EXAMPLE 1

4-Nitronaphthalene-1-carboxylic acid is prepared according to the method of G. J. Leuck and R. P. Perkins, J. Amer. Chem. Soc., 51, 1831 (1929).

14.67 g of the hydrochloride of the methyl ester of L-methionine, 9.93 g of 1-hydroxybenzotriazole, 7.5 cm$^3$ of triethylamine and 15.16 g of dicyclohexylcarbodiimide are added to a solution of 14.5 g of 4-nitronaphthalene-1-carboxylic acid in 290 cm$^3$ of chloroform and 87 cm$^3$ of dimethylformamide. The reaction mixture is stirred for 3 days at a temperature in the region of 20° C. and then filtered through sintered glass, washed with 200 cm$^3$ of dichloromethane. The organic solution is washed twice with 200 cm$^3$ of a 10% (w/v) aqueous sodium bicarbonate solution, then with a 10% (w/v) aqueous citric acid solution, with distilled water and then with a saturated aqueous sodium chloride solution. The organic phase is dried over magnesium sulphate, filtered and then concentrated to dryness under reduced pressure. 24.5 g of an oil are obtained, which oil is purified by chromatography on silica, elution being carried out with a cyclohexane/ethyl acetate (1/1 by volume) mixture. 19 g of the methyl ester of N-[4-nitronaphthyl-1-carbonyl]-L-methionine are thus obtained in the form of an orange oil.

29.5 g of tin(II) chloride dihydrate are added to a solution of 9.5 g of the methyl ester of N-[4-nitronaphthyl-1-carbonyl]-L-methionine in 140 cm$^3$ of ethanol. The reaction mixture is stirred for 30 minutes at a temperature in the region of 70° C. and then cooled to a temperature in the region of 20° C. The reaction mixture is poured onto ice and then brought to a pH in the region of 7–8 by addition of a 5% (w/v) aqueous sodium hydrogencarbonate solution. The mixture obtained is filtered through sintered glass covered with celite. 1000 cm$^3$ of ethyl acetate are added. The organic phase is separated by settling and washed with 800 cm$^3$ of distilled water. The organic phase is dried over magnesium sulphate, filtered and concentrated to dryness under reduced pressure. The orange oil obtained is purified by chromatography on silica, elution being carried out with a cyclohexane/ethyl acetate (1/1 by volume) mixture. 3.6 g of the methyl ester of N-[4-aminonaphthyl-1-carbonyl]-L-methionine are thus obtained in the form of an oil, the characteristics of which are as follows:

mass spectrum (EI): M/Z=332 (M$^+$)

9.71 g of S-triphenylmethyl-N-(tert-butoxycarbonyl) cysteinal, prepared according to the process described in Patent EP-0,618,221, 0.62 cm$^3$ of acetic acid, molecular sieve (3 Å) and then 2.04 g of sodium cyanoborohydride are added to a solution of 3.6 g of the methyl ester of N-[4-aminonaphthyl-1-carbonyl]-L-methionine in 240 cm$^3$ of acetonitrile. The reaction mixture is stirred for 3 days at a temperature in the region of 20° C. and then filtered through sintered glass covered with celite. The sintered glass is washed with ethyl acetate. The filtrate is concentrated under reduced pressure. A foam is obtained, which foam is purified by chromatography on silica, elution being carried out with a cyclohexane/ethyl acetate (7/3 by volume) mixture. 1.3 g of the methyl ester of N-[4-(2(R)-tert-butoxycarbonylamino-3-(triphenylmethylthio)propylamino) naphthy-1-carbonyl]-L-methionine are obtained in the form of a yellow solid, the characteristics of which are as follows:

mass spectrum (LSIMS): M/Z=764 (MH$^+$) 0.071 g of lithium hydroxide hydrate is added to a solution of 0.63 g of the methyl ester of N-[4-(2(R)-tert-butoxycarbonylamino-3-(triphenylmethylthio)propylamino)naphthyl- 1-carbonyl]-L-methionine in 3.3 cm$^3$ of distilled water and 13 cm$^3$ of tetrahydrofuran. The solution is stirred for 20 hours at a temperature in the region of 20° C. and then concentrated under reduced pressure. The residue is dissolved in distilled water and then brought to pH=2 by addition of an N hydrochloric acid solution. The aqueous phase is extracted 3 times with 25 cm$^3$ of ethyl acetate. The organic phases are combined, washed with a saturated aqueous sodium chloride solution, dried over magnesium sulphate, filtered and concentrated to dryness under reduced pressure. 0.6 g of N-[4-(2(R)-tert-butoxycarbonylamino-3-(triphenylmethylthio) propylamino)naphthyl-1-carbonyl]-L-methionine is obtained in the form of a foam.

0.15 cm$^3$ of triethylsilane and 0.61 cm$^3$ of trifluoroacetic acid are added, at a temperature in the region of 20° C., to a mixture of 0.6 g of N-[4-(2(R)-tert-butoxycarbonylamino-3-(triphenylmethylthio)propylamino)naphthyl-1-carbonyl]-L-methionine in 3.8 cm$^3$ of dichloromethane. The reaction mixture is stirred for 2 hours at a temperature in the region of 20° C. and then concentrated under reduced pressure. The residue is triturated 3 times with 15 cm³ of ethyl ether and then dried under reduced pressure. The residue is purified by high performance liquid chromatography (C18 phase), elution being carried out with an acetonitrile/water mixture containing 0.1% of trifluoroacetic acid. 0.13 g of the trifluoroacetate of N-[4-(2(R)-amino-3-mercaptopropylamino) naphthyl-1-carbonyl]-L-methionine is obtained in the form of a powder, the characteristics of which are as follows:

Proton nuclear magnetic resonance spectrum (400 MHz, d6-$(CD_3)_2SO$, δ in ppm): 2.05 (mt, 2H, $CH_2$), 2.08 (s, 3H, $SCH_3$), 2.60 (mt, 2H, $SCH_2$), 2.86 (mt, 2H, $CH_2S$), from 3.40 to 3.70 (mt, 3H, $NCH_2CHN$), 4.55 (mt, 1H, CHCOO), 6.65 (d, J=8 Hz, 1H, H at 3), 6.69 (mt, 1H, ArNH), from 7.40 to 7.60 (mt, 2H, H at 6 and H at 7), 7.60 (d, J=8 Hz, 1H, H at 2), 8.10 (unresolved peak, 3H, $NH_3^+CF_3COO^-$), 8.20 and 8.42 (2 d, J=8 Hz, each 1H, H at 5 and H at 8), 8.48 (d, J=7.5 Hz, 1H, ArCONH), 12.65 (unresolved peak, 1H, COOH).

Elemental analysis: $C_{19}H_{25}N_3O_3S_2.1.2CF_3CO_2H$: Calculated (%):C=47.2, H=4.85, N=7.7, S=11.78 Found (%): C=46.6, H=4.6, N=7.5, S=11.4.

EXAMPLE 2

By carrying out the process as in Example 1 for the preparation of the trifluoroacetate of N-[4-(2(R)-amino-3-mercaptopropylamino)naphthyl-1-carbonyl]-L-methionine, but from 0.65 g of the methyl ester of N-[4-(2(R)-tert-butoxycarbonylamino-3-(triphenylmethylthio)propylamino) naphthyl-1-carbonyl]-L-methionine, 0.07 g of the trifluoroacetate of the methyl ester of N-[4-(2(R)-amino-3-mercaptopropylamino)naphthyl-1-carbonyl]-L-methionine is obtained, the characteristics of which are as follows:

Proton nuclear magnetic resonance spectrum (300 MHz, d6-$(CD_3)_2SO$, δ in ppm): 2.07 (mt, 2H, $CH_2$), 2.09 (s, 3H, $SCH_3$), 2.63 (mt, 2H, $SCH_2$), 2.90 (mt, 2H, $CH_2S$), from 3.40 to 3.70 (mt, 3H, $NCH_2CHN$), 3.70 (s, 3H, $COOCH_3$), 4.62 (mt, 1H, CHCOO), 6.65 (d, J=8 Hz, 1H, H at 3), 6.73 (mt, 1H, ArNH), from 7.40 to 7.60 (mt, 2H, H at 6 and H at 7), 7.63 (d, J=8 Hz, 1H, H at 2), 8.13 (unresolved peak, 3H, $NH_3^+CF_3COO^-$), 8.22 and 8.37 (2 d, J=8 Hz, each 1H, H at 5 and H at 8), 8.64 (d, J=7.5 Hz, 1H, ArCONH).

Elemental analysis: $C_{20}H_{27}N_3O_3S_2.1.2CF_3CO_2H$ Calculated (%):C=48.19, H=5.09, N=7.52, S=11.48 Found (%): C=48.6, H=5.0, N=7.6, S=11.5.

EXAMPLE 3

The methyl ester of N-[4-nitronaphthyl-1-thiocarbonyl]-L-methionine is prepared, with a yield of 35%, with Lawesson's reagent, according to the method of Ocain and Rich, J. Med. Chem., 1988, 31 (11), 2195 (1988), from the methyl ester of N-[4-nitronaphthyl-1-carbonyl]-L-methionine.

3.28 g of tin(II) chloride dihydrate are added to a solution of 1.1 g of the methyl ester of N-[4-nitronaphthyl-1-thiocarbonyl]-L-methionine in 5.8 cm³ of ethanol and 23 cm³ of ethyl acetate. The reaction mixture is stirred for 3 hours at a temperature in the region of 70° C. and then cooled to a temperature in the region of 20° C. The reaction mixture is poured onto ice and then brought to a pH in the region of 7–8 by addition of a 5% (w/v) aqueous sodium hydrogencarbonate solution. The mixture obtained is filtered through sintered glass covered with celite. The organic phase is separated by settling and the aqueous phase is extracted successively with 2 times 20 cm³ of ethyl acetate. The organic phases are combined, dried over magnesium sulphate, filtered and concentrated to dryness under reduced pressure. 0.74 g of the methyl ester of N-[4-aminonaphthyl-1-thiocarbonyl]-L-methionine is thus obtained in the form of a yellow powder.

1.9 g of S-triphenylmethyl-N-(tert-butoxycarbonyl) cysteinal, prepared according to the process described in Patent EP-0,618,221, 0.12 cm³ of concentrated acetic acid, molecular sieve (3 Å) and then 0.4 g of sodium cyanoborohydride are added to a solution of 0.74 g of the methyl ester of N-[4-aminonaphthyl-1-thiocarbonyl]-L-methionine in 48 cm³ of acetonitrile. The reaction mixture is stirred for 48 hours at a temperature in the region of 20° C. and then filtered through sintered glass covered with celite. The sintered glass is washed with acetonitrile. The filtrate is concentrated under reduced pressure. An orange oil is obtained, which oil is purified by chromatography on silica, elution being carried out with a cyclohexane/ethyl acetate (6/4 by volume) mixture. 0.66 g of the methyl ester of N-[4-(2(R)-tert-butoxycarbonylamino-3-(triphenylmethylthio)-propylamino)naphthyl-1-thiocarbonyl]-L-methionine is obtained in the form of a yellow oil.

mass spectrum (LSIMS): M/Z=780 ($MH^+$), M/Z=243 ($CPh_3$)

0.61 cm³ of trifluoroacetic acid is added, at a temperature in the region of 20° C., to 0.61 g of the methyl ester of N-[4-(2(R)-tert-butoxycarbonylamino-3-(triphenylmethylthio)propylamino)naphthyl-1-thiocarbonyl]-L-methionine in 3.85 cm³ of dichloromethane and 0.15 cm³ of triethylsilane. The reaction mixture is stirred for 2 hours at a temperature in the region of 20° C. and then concentrated under reduced pressure. The residue is triturated successively with 3 times 5 cm³ of ethyl ether and then dried under reduced pressure. The compounds are purified and separated by high performance liquid chromatography (C18 phase), elution being carried out with an acetonitrile/water mixture containing 0.1% of trifluoroacetic acid. 0.013 g of the ditrifluoroacetate of the dimethyl ester of di{N-[4-(2(R)-amino-3-mercaptopropylamino)naphthyl-1-thiocarbonyl]-L-methionine} is obtained in the form of a powder.

The ditrifluoroacetate of the dimethyl ester of di{N-[4-(2(R)-amino-3-mercaptopropylamino)naphthyl-1-thiocarbonyl]-L-methionine} has the following characteristics:

proton nuclear magnetic resonance spectrum (250 MHz, d6-$(CD_3)_2SO$, δ in ppm): 2.12 (s, 3H, $SCH_3$), 2.20 (mt, 2H, $CH_2$), 2.63 (mt, 2H, $SCH_2$), 3.10 and 3.22 (2 mts, each 1H, $CH_2S$), from 3.50 to 3.90 (mt, 3H, $NCH_2CHN$), 3.78 (s, 3H, $COOCH_3$), 5.28 (mt, 1H, CHCOO), 6.65 (d, J=8 Hz, 1H, H3), 6.69 (t, J=6 Hz, 1H, ArNH), 7.38 (d, J=8 Hz, 1H, H2), from 7.40 to 7.65 (mt, 2H, H6 and H7), from 8.10 to 8.35 (mt, 5H, $NH_3^+CF_3COO^-$, H5 and H8), 10.62 (d, J=7.5 Hz, 1H, ArCSNH).

EXAMPLE 4

6-Nitronaphthalene-1-carboxylic acid and 3-nitronaphthalene-1-carboxylic acid are prepared, in a ratio of 80/20, according to the method of T. Nakayama et al., Chem. Pharm. Bull., 32, 3968 (1984).

9.9 g of the hydrochloride of the methyl ester of (L)-methionine, 6.8 g of 1-hydroxybenzotriazole, 5 cm³ of triethylamine and 10.3 g of dicyclohexylcarbodiimide are added to a solution of a mixture of 9.84 g of 6-nitronaphthalene-1-carboxylic acid and 3-nitronaphthalene-1-carboxylic acid in 200 cm³ of chloroform and 60 cm³ of dimethylformamide. The reaction mixture is stirred for 2 days at a temperature in the region of 20° C. and then filtered through sintered glass, washed with 50 cm³ of chloroform. The organic solution is washed twice with 200 cm³ of a 10% (w/v) aqueous sodium bicarbonate solution, then with a 10% (w/v) aqueous citric acid solution, with distilled water and then with a saturated aqueous sodium chloride solution. The organic phase is dried over magnesium sulphate, filtered and then concentrated to dryness under reduced pressure. 13.3 g of an oil are obtained, which oil is purified by chromatography on silica, elution being carried out with a cyclohexane/ethyl acetate (1/1 by volume) mixture. 0.64 g of the methyl ester of N-[6-nitronaphthyl-1-carbonyl]-L-methionine is thus obtained in the form of a solid, as well as 3.7 g of a mixture of the methyl ester of N-[6-nitronaphthyl-1-carbonyl]-L-methionine and the methyl ester of N-[3-nitronaphthyl-1-carbonyl]-L-methionine in a 70/30 ratio.

9.35 g of tin(II) chloride dihydrate are added to a solution of 3 g of a mixture of the methyl esters of N-[6-nitronaphthyl-1-carbonyl]-L-methionine and N-[3-nitronaphthyl-1-carbonyl]-L-methionine in 140 cm³ of ethanol. The reaction mixture is stirred for 1 hour at a temperature in the region of 70° C. and then cooled to a temperature in the region of 20° C. 140 cm³ of ethyl acetate are added. The reaction mixture is poured onto ice and then brought to a pH in the region of 7–8 by addition of a 5% (w/v) aqueous sodium hydrogencarbonate solution. The mixture obtained is filtered through sintered glass covered with celite. The organic phase is separated by settling and the aqueous phase is extracted 3 times with 400 cm³ of ethyl acetate. The organic phases are combined, dried over magnesium sulphate, filtered and concentrated to dryness under reduced pressure. 3 g of an oil are thus obtained, which oil is purified by chromatography on silica, elution being carried out with a cyclohexane/ethyl acetate (1/1 by volume) mixture. 1.82 g of a mixture of the methyl esters of N-[6-aminonaphthyl-1-carbonyl]-L-methionine and N-[3-aminonaphthyl-1-carbonyl]-L-methionine, in a 70/30 ratio, are thus obtained in the form of an oil.

mass spectrum (DCI, NH₃): M/Z=333 (MH⁺)

4.16 g of S-triphenylmethyl-N-(tert-butoxycarbonyl) cysteinal, prepared according to the process described in Patent EP-0,618,221, 0.56 cm³ of concentrated acetic acid, molecular sieve (3 Å) and then 0.58 g of sodium cyanoborohydride are added to a solution of 1 g of a mixture of the methyl esters of N-[6-aminonaphthyl-1-carbonyl]-L-methionine and N-[3-aminonaphthyl-1-carbonyl]-L-methionine in 65 cm³ of methanol. The reaction mixture is stirred for 48 hours at a temperature in the region of 20° C. and then filtered through sintered glass covered with celite. The sintered glass is washed with acetonitrile. The filtrate is concentrated under reduced pressure. An orange oil is obtained, which oil is purified by chromatography on silica, elution being carried out with a cyclohexane/ethyl acetate (7/3 by volume) mixture. 1.67 g of a mixture of the methyl esters of N-[6-(2(R)-tert-butoxycarbonylamino-3-(triphenylmethylthio)propylamino)naphthy-1-carbonyl]-L-methionine and N-[3-(2(R)-tert-butoxycarbonylamino-3-(triphenylmethylthio)propylamino)naphthyl-1-carbonyl]-L-methionine, in a 70/30 ratio, are obtained in the form of a yellow oil.

0.06 g of lithium hydroxide hydrate is added to a solution of 0.45 g of a mixture of the methyl esters of N-[6-(2(R)-tert-butoxycarbonylamino-3-(triphenylmethylthio) propylamino)naphthyl-1-carbonyl]-L-methionine and N-[3-(2(R)-tert-butoxycarbonylamino-3-(triphenylmethylthio)-propylamino)naphthyl-1-carbonyl]-L-methionine in 2 cm³ of distilled water and 20 cm³ of tetrahydrofuran. The solution is stirred for 20 hours at a temperature in the region of 20° C. and then concentrated under reduced pressure. 0.4 g of a mixture of N-[6-(2(R)-tert-butoxycarbonylamino-3-(triphenylmethylthio)-propylamino)naphthyl-1-carbonyl]-L-methionine and N-[3-(2(R)-tert-butoxycarbonylamino-3-(triphenylmethylthio)-propylamino)naphthyl-1-carbonyl]-L-methionine, in a 70/30 ratio, is obtained in the form of a foam.

2.25 cm³ of ethanedithiol and then 22.5 cm³ of trifluoroacetic acid are added, at a temperature in the region of 0° C., to a mixture of 0.4 g of N-[6-(2(R)-tert-butoxycarbonylamino-3-(triphenylmethylthio)propylamino) naphthyl-1-carbonyl]-L-methionine and N-[3-(2(R)-tert-butoxycarbonylamino-3-(triphenylmethylthio)-propylamino)naphthyl-1-carbonyl]-L-methionine in 2.2 cm³ of distilled water. The reaction mixture is stirred for 2 hours at a temperature in the region of 20° C. and then concentrated under reduced pressure. The residue is triturated 3 times with 15 cm³ of ethyl ether and then dried under reduced pressure. The residue is purified by high performance liquid chromatography (C18 phase), elution being carried out with an acetonitrile/water mixture containing 0.1% of trifluoroacetic acid. 0.04 g of the trifluoroacetate of N-[3-(2(R)-amino-3-mercaptopropylamino)naphthyl-1-carbonyl]-L-methionine is obtained in the form of a powder, the characteristics of which are as follows:

proton nuclear magnetic resonance spectrum (250 MHz, d6-(CD₃)₂SO, δ in ppm): 2.07 (mt, 2H, CH₂), 2.10 (s, 3H, SCH₃), 2.60 (mt, 2H, SCH₂), 2.90 (limiting AB, 2H, CH₂S), from 3.35 to 3.60 (mt, 3H, NCH₂CHN), 4.60 (mt, 1H, CHCOO), 6.32 (unresolved peak, 1H, ArNH), 6.95 (d, J=2 Hz, 1H, H4), 7.10 (d, J=2 Hz, 1H, H2), 7.22 (broad t, J=8 Hz, 1H, H7), 7.40 (broad t, J=8 Hz, 1H, H6), 7.66 (broad d, J=8 Hz, 1H, H5), 7.97 (broad d, J=8 Hz, 1H, H8), 8.10 (unresolved peak, 3H, NH₃⁺CF3COO⁻), 8.80 (d, J=7.5 Hz, 1H, ArCONH), 12.70 (broad unresolved peak, 1H, COOH).

elemental analysis: C₁₉H₂₅N₃O₃S₂.1.25CF₃CO₂H: Calculated (%):C=46.9, H=4.82, N=7.6, S=11.6 Found (%): C=46.8, H=4.8, N=7.7, S=11.9.

EXAMPLE 5

By carrying out the process as in Example 4 for the preparation of the trifluoroacetate of N-[3-(2(R)-amino-3-mercaptopropylamino)naphthyl-1-carbonyl]-L-methionine, but from 0.6 g of a mixture of the methyl esters of N-[6-(2(R)-tert-butoxycarbonylamino-3-(triphenylmethylthio) propylamino)naphthyl-1-carbonyl]-L-methionine and N-[3-(2(R)-tert-butoxycarbonylamino-3-(triphenylmethylthio)-propylamino)naphthyl-1-carbonyl]-L-methionine, 0.05 g of the trifluoroacetate of the methyl ester of N-[3-(2(R)-amino-3-mercaptopropylamino)naphthyl-1-carbonyl]-L-methionine is obtained, the characteristics of which are as follows:

proton nuclear magnetic resonance spectrum (400 MHz, d6-(CD₃)₂SO with the addition of a few drops of d4-CD₃COOD, δ in ppm): 2.07 (s, 3H, SCH₃), 2.07 (mt, 2H, CH₂), 2.60 (mt, 2H, SCH₂), 2.82 and 2.90 (2 dd, J=15 and 6 Hz, each 1H, CH₂S), from 3.35 to 3.55 (mt, 3H, NCH₂CHN), 3.72 (s, 3H, COOCH₃), 4.68 (dd, J=10 and 4.5 Hz, 1H, CHCOO), 6.95 (d, J=2 Hz, 1H, H4), 7.10 (d, J=2 Hz, 1H, H2), 7.20 (t, J=8 Hz, 1H, H7), 7.38 (t, J=8 Hz, 1H, H6), 7.60 (d, J=8 Hz, 1H, H5), 7.95 (d,J=8 Hz, 1H, H8).

elemental analysis: C₂₀H₂₇N₃O₃S₂.1.25CF₃CO₂H: Calculated (%):C=47.9, H=5.05, N=7.4, S=11.4 Found (%): C=47.9, H=5.3, N=7.6, S=11.4.

EXAMPLE 6

The mixture of the methyl esters of N-[6-nitronaphthyl-1-thiocarbonyl]-L-methionine and N-[3-nitronaphthyl-1-thiocarbonyl]-L-methionine, in a 70/30 ratio, is prepared with a yield of 50% with Lawesson's reagent, according to the method of Ocain and Rich, J. Med. Chem., 31 (11), 2195 (1988), from a mixture of the methyl ester of N-[6-nitronaphthyl-1-carbonyl]-L-methionine and the methyl ester of N-[3-nitronaphthyl-1-carbonyl]-L-methionine, in a 70/30 ratio.

mass spectrum (DCI; NH3): M/Z=379 (MH$^+$)

5.87 g of tin(II) chloride dihydrate are added to a solution of 2 g of the mixture of the methyl esters of N-[6-nitronaphthyl-1-thiocarbonyl]-L-methionine and N-[3-nitronaphthyl-1-thiocarbonyl]-L-methionine in 10 cm$^3$ of ethanol. The reaction mixture is stirred for 30 minutes at a temperature in the region of 70° C. and then cooled to a temperature in the region of 20° C. 40 cm$^3$ of ethyl acetate are added. The reaction mixture is poured onto ice and then brought to a pH in the region of 7–8 by addition of a 5% (w/v) aqueous sodium hydrogencarbonate solution. The mixture obtained is filtered through sintered glass covered with celite. The organic phase is separated by settling and the aqueous phase is extracted successively 3 times with 150 cm$^3$ of ethyl acetate. The organic phases are combined, dried over magnesium sulphate, filtered and concentrated to dryness under reduced pressure. 1.8 g of the mixture of the methyl esters of N-[6-aminonapbthyl-1-thiocarbonyl]-L-methionine and N-[3-aminonaphthyl-1-thiocarbonyl]-L-methionine, in a 70/30 ratio, are thus obtained in the form of an oil.

6.9 g of S-triphenylmethyl-N-(tert-butoxycarbonyl) cysteinal, prepared according to the process described in Patent EP-0,618,221, 0.91 cm$^3$ of concentrated acetic acid, molecular sieve (3 Å) and then 0.97 g of sodium cyanoborohydride are added to a solution of 1.8 g of the mixture of the methyl esters of N-[6-aminonaphthyl-1-thiocarbonyl]-L-methionine and N-[3-aminonaphthyl-1-thiocarbonyl]-L-methionine in 70 cm$^3$ of acetonitrile. The reaction mixture is stirred for 24 hours at a temperature in the region of 20° C. and then filtered through sintered glass covered with celite. The sintered glass is washed with acetonitrile. The filtrate is concentrated under reduced pressure. A foam is obtained, which foam is purified by chromatography on silica, elution being carried out with a dichloromethane/ethyl acetate (95/5 by volume) mixture. 1.2 g of a mixture of the methyl esters of N-[6-(2(R)-tert-butoxycarbonylamino-3-(triphenylmethylthio)propylamino)naphthyl-1-thiocarbonyl]-L-methionine and N-[3-(2(R)-tert-butoxycarbonylamino-3-(triphenylmethylthio)propylamino)naphthyl-1-thiocarbonyl]-L-methionine, in a 70/30 ratio, are obtained in the form of a yellow solid.

0.17 g of lithium hydroxide hydrate is added to a solution of 0.9 g of the mixture of the methyl esters of N-[6-(2(R)-tert-butoxycarbonylamino-3-(triphenylmethylthio) propylamino)naphthyl-1-thiocarbonyl]-L-methionine and N-[3-(2(R)-tert-butoxycarbonylamino-3-(triphenylmethylthio)-propylamino)naphthyl-1-thiocarbonyl]-L-methionine in 2.25 cm$^3$ of distilled water and 22.5 cm$^3$ of tetrahydrofuran. The solution is stirred for 20 hours at a temperature in the region of 20° C. and then concentrated under reduced pressure. 0.88 g of a mixture of N-[6-(2(R)-tert-butoxycarbonylamino-3-(triphenylmethylthio)propylamino)naphthyl-1-thiocarbony] -L-methionine and N-[3-(2(R)-tert-butoxycarbonylamino-3-(triphenylmethylthio)-propylamino)naphthyl-1-thiocarbonyl]-L-methionine is obtained in the form of a foam.

2.5 cm$^3$ of trifluoroacetic acid are added, at a temperature in the region of 20° C., to 0.4 g of a mixture of N-[6-(2(R)-tert-butoxycarbonylamino-3-(triphenylmethylthio) propylamino)naphthyl-1-thiocarbonyl]-L-methionine and N-[3-(2(R)-tert-butoxycarbonylamino-3-(triphenylmethylthio)-propylamino)naphthyl-1-thiocarbonyl]]-L-methionine in 2.5 cm$^3$ of dichloromethane and 0.1 cm$^3$ of triethylsilane. The reaction mixture is stirred for 1 hour at a temperature in the region of 20° C. and then concentrated under reduced pressure. The residue is triturated successively with 3 times 5 cm$^3$ of hexane, 3 times 5 cm$^3$ of pentane and 3 times 5 cm$^3$ of ethyl ether and then dried under reduced pressure. The compounds are purified and separated by high performance liquid chromatography (C18 phase), elution being carried out with an acetonitrile/water mixture containing 0.1% of trifluoroacetic acid. 0.028 g of the trifluoroacetate of N-[6-(2(R)-amino-3-mercaptopropylamino)naphthyl-1-thiocarbonyl]-L-methionine and 0.012 g of the trifluoroacetate of N-[3-(2 (R)-amino-3-mercaptopropylamino)naphthyl-1-thiocarbonyl]-L-methionine are obtained in the form of powders.

The trifluoroacetate of N-[3-(2(R)-amino-3-mercaptopropylamino)naphthyl-1-thiocarbonyl]-L-methionine has the following characteristics:

proton nuclear magnetic resonance spectrum (400 MHz, d6-(CD$_3$)$_2$SO, at a temperature of 333 K, δ in ppm): 2.15 (s, 3H, SCH$_3$), 2.20 (mt, 2H, CH$_2$), 2.65 (limiting AB, 2H, SCH$_2$), 2.90 (limiting AB, 2H, CH$_2$S), from 3.30 to 3.60 (mt, 3H, NCH$_2$CHN), 5.30 (mt, 1H, CHCOO), 6.15 (broad unresolved peak, 1H, ArNH), 6.95 (d, J=2 Hz, 1H, H4), 7.10 (d, J=2 Hz, 1H, H2), 7.22 (broad t, J=8 Hz, 1H, H7), 7.40 (broad t, J=8 Hz, 1H, H6), 7.66 (broad d, J=8 Hz, 1H, H5), 7.96 (broad d, J=8 Hz, 1H, H8), 8.00 (unresolved peak, 3H, NH$_2$), 10.62 (d, J=7.5 Hz, 1H, ArCSNH).

elemental analysis: C$_{19}$H$_{25}$N$_3$O$_2$S$_3$.1.33CF$_3$CO$_2$H Calculated (%):C=45.2, H=4.6, N=7.3, S=16.7 Found (%): C=45.2, H=4.4, N=7.7, S=16.2.

The inhibitory activity with respect to farnesyl transferase and to farnesylation of the Ras protein may be demonstrated in the following test:

Farnesyl transferase activity is determined by the quantity of [$^3$H]farnesyl transferred from [$^3$H]farnesyl pyrophosphate ([$^3$H]FPP) to the p21 H-Ras protein. The standard reaction mixture is composed, for a final volume of 60 μl, of 50 mM Tris-HCl, 5 mM MgCl$_2$, 5 mM dithiothreitol, 0.2% octyl β-D-glucopyranoside, 200 picomol p21 H-Ras, 4.5 picomol [$^3$H]FPP (activity 61000 dpm/picomol).

Reaction is initiated by adding approximately 5 ng of human farnesyl transferase purified from THP1 cell cultures. After incubation for 20 minutes at 37° C. in a microtitration plate containing 96 1-cm$^3$ wells per plate (Titer Plate®, Beckman), the reaction is stopped by adding 0.4 cm$^3$ of 0.1% SDS in methanol at 0° C. The mixture is then treated with 0.4 cm$^3$ of 30% trichloroacetic acid (TCA) in methanol. The plates are left in ice for 1 hour. The precipitated contents are then retained on Filtermat®, Pharmacia) glass fibre membranes with the filtration unit (Combi Cell Harvester®, Skatron), and rinsed with 6% trichloroacetic acid in distilled water. The membranes are dried in a microwave oven, then impregnated with scintillation medium by melting of Meltilex® (Pharmacia) under hot air, and lastly counted in cpm in a β-Plate counter® (LKB). Each test is repeated 3 times.

The unit of activity is defined as 1 picomole of [$^3$H]FPP transferred to p21 H-Ras in 20 minutes.

The percentage inhibition values are obtained by comparison of the tests with and without inhibitor after deduction of blanks, the $IC_{50}$ values being measured on the basis of the inhibitions obtained with 9 different concentrations using Enzfitter® or Grafit® software.

The activity against cells can be determined in the following way:

The cell line is the THAC line (CCL 39 cells transfected with activated Ha-Ras) according to K. Seuwen et al., EMBO J., 7(1) 161–168 (1988). The cells are cultured in Petri dishes with a diameter of 6 cm containing a DMEM medium, 5% foetal calf serum and 1% G418.

After culturing for 24 hours, the culture medium is changed (with or without the serum) and the product to be studied is added in solution in dimethylformamide (DMF), in the presence or in the absence of DTT (final concentrations of 0.5% in DMF and 0.1 mM in DTT). After culturing for 24 hours at 37° C., the cells are lysed in 1 cm³ of lysis buffer (20 mM Tris, HCl, 1% Triton X114, 5 mM $MgCl_2$, 7 mM DTT, 150 mM NaCl, pH=7.4). The lysates are clarified by centrifuging at 4000 revolutions/minute for 10 minutes. Extraction with Triton X114 makes it possible to separate the farnesylated Ras protein from the non-farnesylated Ras protein (C. Bordier, J. Biol. Chem., 256 (4), 1604–1607 (1981)]. The farnesylated Ras protein, which is more hydrophobic, is found in the detergent phase whereas the non-farnesylated Ras protein is in the aqueous phase. The samples are denatured by heating at 95° C. in the denaturation buffer for electrophoresis and deposited on a 14% polyacrylamide gel. When the dye reaches the bottom of the gel, the proteins of the gel are transferred onto a PVDF membrane. The Ras protein is visualized by the Western blot technique: the membrane is incubated with an anti-Ras specific monoclonal antibody (pan-Ras Ab3, Oncogene Science) and then with protein A labelled with $^{125}I$. After autoradiography, the bands are identified, cut out and counted in a γ counter. The radioactivity of the bands corresponding to farnesylated Ras and to non-farnesylated Ras makes it possible to determine the percentage of inhibition of farnesylation of the Ras protein.

The results obtained are collated in Table I.

TABLE I

| PRODUCT | Inhibitory activity $IC_{50}$ nM | % of inhibition against cells (THAC) |
| --- | --- | --- |
| Example 1 | 23 | |
| Example 2 | 100 | 40% at 10 µM |
| Bxample 4 | 31 | |
| Example 5 | 300 | |
| Example 6 | 55 | |

The new products of general formula (I) can be in the form of non-toxic and pharmaceutically acceptable salts. These non-toxic salts comprise the salts with inorganic acids (hydrochloric, sulphuric, hydrobromic, phosphoric and nitric acids) or with organic acids (acetic, propionic, succinic, maleic, hydroxymaleic, benzoic, fumaric, methanesulphonic, trifluoroacetic or oxalic acid), or with inorganic bases (sodium hydroxide, potassium hydroxide, lithium hydroxide, calcium hydroxide) or organic bases (tertiary amines such as triethylamine, piperidine, benzylamine), depending on the nature of the $R_1$ and R symbols of the product of general formula (I).

The present invention also relates to pharmaceutical compositions containing at least one product of general formula (I), in combination with one or more pharmaceutically acceptable diluents or adjuvants, which may be either inert or physiologically active.

These compositions may be administered orally, parenterally or rectally.

The compositions for oral administration comprise tablets, pills, powders or granules. In these compositions, the active product according to the invention is mixed with one or more inert diluents such as sucrose, lactose or starch. These compositions can comprise substances other than diluents, for example lubricants such as magnesium stearate.

As liquid compositions for oral administration, solutions, suspensions, syrups, elixirs and pharmaceutically acceptable emulsions, containing inert diluents such as water or liquid paraffm, may be used. These compositions can also comprise substances other than diluents, for example wetting, sweetening or flavouring products.

The compositions according to the invention for parenteral administration can be sterile solutions, aqueous or non-aqueous, suspensions or emulsions. As solvent or vehicle, propylene glycol, a polyethylene glycol, vegetable oils, especially olive oil, or injectable organic esters, for example ethyl oleate, may be employed. These compositions can also contain adjuvants, especially wetting, emulsifying and dispersing agents. The sterilization may be carried out in several ways, for example using a bacteriological filter, by incorporating sterilizing agents in the composition or by heating. They may also be prepared in the form of sterile solid compositions which can be dissolved at the time of use in sterile water or any other sterile injectable medium.

The compositions for rectal administration are suppositories which can contain, besides the active product, excipients such as cocoa butter.

The compositions according to the invention are especially useful in human therapy in the treatment of cancers of various origins.

In human therapy, the doses depend on the effect sought, the period of treatment and factors specific to the subject to be treated.

Generally, in man, the doses are between 0.1 and 20 mg/kg per day via the intraperitoneal route.

A composition according to the invention is illustrated in the following example.

EXAMPLE 200 mg of the product obtained in Example 1 are dissolved in 100 cm³ of physiological serum. The solution obtained is divided up aseptically into 10 cm³ phials.

The phials are administered as a single injection or by perfusion.

We claim:

1. The products of general formula:

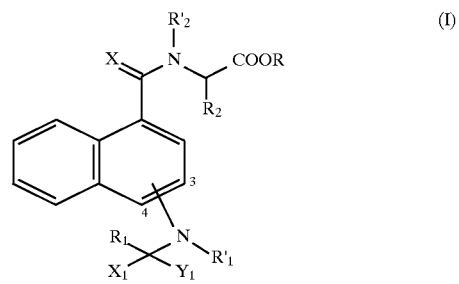

in which:

$R_1$ represents a radical of general formula $Y-S-A_1-$ in which Y represents a hydrogen atom or an amino acid residue or a fatty acid residue or an alkyl or alkoxycarbonyl radical or an R$_4$—S— radical in which R$_4$ represents an alkyl radical containing 1 to 4 carbon atoms, optionally substituted by a phenyl radical, or a radical of general formula:

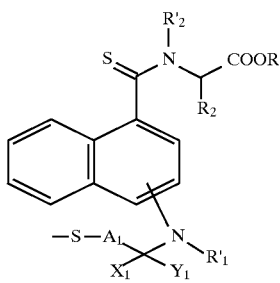

(II)

in which A$_1$, X, X$_1$, Y$_1$, R'$_1$, R$_2$, R'$_2$ and R are defined as below, and A$_1$ represents a straight or branched alkylene radical containing 1 to 4 carbon atoms, optionally substituted at the position α to the >C(X$_1$)(Y$_1$) group by an amino radical, an alkylamino radical containing 1 to 6 straight- or branched-chain carbon atoms, a dialkylamino radical in which each alkyl part contains 1 to 6 straight- or branched-chain carbon atoms, an alkanoylamino radical containing 1 to 6 straight- or branched-chain carbon atoms or an alkoxycarbonylamino radical in which the alkyl part contains 1 to 6 straight- or branched-chain carbon atoms, X$_1$ and Y$_1$ each represent a hydrogen atom or form, together with the carbon atom to which they are bonded, a >C=O group, R'$_1$ represents a hydrogen atom or a straight or branched alkyl radical containing 1 to 6 carbon atoms, X represents an oxygen or sulphur atom, R$_2$ represents a straight or branched alkyl, alkenyl or alkynyl radical containing 1 to 6 carbon atoms, optionally substituted by a hydroxyl radical, an alkoxy radical containing 1 to 4 carbon atoms, a mercapto radical, an alkylthio radical containing 1 to 4 carbon atoms, an alkylsulphinyl radical containing 1 to 4 carbon atoms or an alkylsulphonyl radical containing 1 to 4 carbon atoms, it being understood that, when R$_2$ represents an alkyl radical substituted by a hydroxyl radical, R$_2$ can form a lactone with the carboxyl radical at the α position, R'$_2$ represents a hydrogen atom or a straight or branched alkyl radical containing 1 to 6 carbon atoms, and R represents a hydrogen atom or an alkyl radical containing 1 to 6 carbon atoms, optionally substituted by a radical of the type alkoxy containing 1 to 4 carbon atoms, alkylthio containing 1 to 4 carbon atoms, alkylsulphinyl containing 1 to 4 carbon atoms, alkylsulphonyl containing 1 to 4 carbon atoms, phenyl, phenoxy, phenylthio, phenylsulphinyl, phenylsulphonyl, alkylamino containing 1 to 4 carbon atoms, dialkylamino in which each alkyl part contains 1 to 4 carbon atoms, or a phenyl radical, optionally substituted by one or a number of atoms or radicals chosen from halogen atoms and alkyl, alkyloxy, alkylthio or alkanoyl radicals, it being understood that the radical

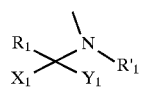

is in the 3- or 4-position of the naphthyl ring.

2. The products according to claim 1 in which:

R$_1$ represents a radical of formula Y—S—A$_1$— in which Y represents a hydrogen atom or a lysine residue or a fatty acid residue containing up to 20 carbon atoms and A$_1$ represents an ethylene or propylene radical optionally substituted by an amino radical, X$_1$ and Y$_1$ each represent a hydrogen atom or form, together with the carbon atom to which they are bonded, a >C=O group, R'$_1$ represents a hydrogen atom or a methyl radical, X represents an oxygen atom, R$_2$ represents an alkyl radical containing 1 to 4 carbon atoms, optionally substituted by a hydroxyl, metboxy, mercapto, methylthio, methylsulphinyl or methylsulphonyl radical, R'$_2$ represents a hydrogen atom or a methyl radical, and R represents a hydrogen atom or an alkyl radical containing 1 to 4 carbon atoms, optionally substituted by an alkoxy radical, or a phenyl radical.

3. The products according to claim 1 in which:

R$_1$ represents a radical of formula Y—S—A$_1$— in which Y represents a hydrogen atom and A$_1$ represents an ethylene or propylene radical optionally substituted by an amino radical, X$_1$ and Y$_1$ each represent a hydrogen atom or form, together with the carbon atom to which they are bonded, a >C=O group, R'$_1$ represents a hydrogen atom, X represents an oxygen atom, R$_2$ represents a methyl, ethyl, propyl or butyl radical optionally substituted by a hydroxyl, methoxy, mercapto or methylthio radical, R'$_2$ represents a hydrogen atom, and R represents a hydrogen atom or an alkyl radical containing 1 to 4 carbon atoms.

4. The products according to claim 1 in which R$_1$ represents a 2-mercaptoethyl or 1-amino-2-mercaptoethyl radical, X$_1$ and Y$_1$ each represent a hydrogen atom or form, together with the carbon atom to which they are bonded, a >C=O group, R'$_1$ represents a hydrogen atom, X represents an oxygen atom, R$_2$ represents an n-butyl or 2-(methylthio) ethyl radical and R'$_2$ represents a hydrogen atom, and R represents a hydrogen atom or a methyl radical.

5. Pharmaceutical composition, characterized in that it contains a sufficient amount of the product according to claim 1 in combination with one or a number of inert or physiologically active pharmaceutically acceptable diluents or adjuvants.

6. Pharmaceutical composition, characterized in that it contains a sufficient amount of the product according to claim 2 in combination with one or a number of inert or physiologically active pharmaceutically acceptable diluents or adjuvants.

7. Pharmaceutical composition, characterized in that it contains a sufficient amount of the product according to claim 3 in combination with one or a number of inert or physiologically active pharmaceutically acceptable diluents or adjuvants.

8. Pharmaceutical composition, characterized in that it contains a sufficient amount of the product according to claim 4 in combination with one or a number of inert or physiologically active pharmaceutically acceptable diluents or adjuvants.

* * * * *